United States Patent [19]

Bell et al.

[11] Patent Number: 5,756,497
[45] Date of Patent: May 26, 1998

[54] TOCOLYTIC OXYTOCIN RECEPTOR ANTAGONISTS

[75] Inventors: Ian M. Bell, Harleysville; Roger M. Freidinger, Lansdale; Peter D. Williams, Harleysville, all of Pa.

[73] Assignee: Merck & Co., Inc., Rahway, N.J.

[21] Appl. No.: 807,307

[22] Filed: Feb. 27, 1997

[51] Int. Cl.⁶ .................... C07D 265/18; A61K 31/535
[52] U.S. Cl. .................. 514/230.5; 544/92; 546/346; 546/315; 546/344; 546/153; 546/180; 546/217
[58] Field of Search ...................... 544/92; 514/230.5

[56] References Cited

U.S. PATENT DOCUMENTS 5,665,719  9/1997  Bork et al. .................. 514/227.8

FOREIGN PATENT DOCUMENTS

| 0382185 | 8/1990 | European Pat. Off. . |
|---|---|---|
| 0470514 | 2/1992 | European Pat. Off. . |
| 0620216 | 10/1994 | European Pat. Off. . |
| 0636608 | 2/1995 | European Pat. Off. . |
| 0636609 | 2/1995 | European Pat. Off. . |
| 0636614 | 2/1995 | European Pat. Off. . |
| 0636625 | 2/1995 | European Pat. Off. . |
| 0640592 | 3/1995 | European Pat. Off. . |
| WO93/15051 | 8/1993 | WIPO . |
| WO95/02405 | 1/1995 | WIPO . |
| WO95/9152 | 4/1995 | WIPO . |
| WO95/19773 | 7/1995 | WIPO . |

OTHER PUBLICATIONS

Williams et al Chem. Abstr. vol. 125, Entry 221854 (Abstracting WO 96 22775), 1996.
Serradeil–Legal et al J. Clin. Invest., (1993) 92, 224–231.
Williams et al J. Med. Chem., (1995) 38, 4634–4636.
Imaizumi et al Hypertension (1992) 20, 54–58.
Yamamura et al Science (1991), 252, 572.
Ohnishi et al J. Clin. Pharm., (1993), 33, 230–238.

Primary Examiner—Donald G. Daus
Attorney, Agent, or Firm—Melvin Winokur

[57] ABSTRACT

This invention relates to certain novel benzoxazinone compounds and derivatives thereof, their synthesis, and their use as oxytocin receptor antagonists. One application of these compounds is in the treatment of preterm labor in mammals, especially humans. The ability of the compounds to relax uterine contractions in mammals also makes them useful for treating dysmenorrhea and stopping labor prior to cesarean delivery.

12 Claims, No Drawings

TOCOLYTIC OXYTOCIN RECEPTOR ANTAGONISTS

This is a non-provisional application based on provisional application Ser. No. 60/012,693, filed Mar. 1, 1996.

FIELD OF THE INVENTION

The present invention provides novel compounds, novel compositions, methods of their use and methods of their manufacture; such compounds are generally pharmacologically useful as agents in obstetric and gynecologic therapy in mammals. More specifically, the compounds of the present invention are useful in the treatment of preterm labor, dysmenorrhea and for stopping labor preparatory (i.e., prior) to cesarean delivery.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_{32}$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that an oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. An oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention are also useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, an oxytocin antagonist is more efficacious for treating dysmenorrhea than current regimens. An additional use for the present invention is for the stoppage of labor preparatory to cesarean delivery.

It is, therefore, a purpose of this invention to provide substances which more effectively antagonize the function of oxytocin in disease states in animals, preferably mammals, especially in humans. It is another purpose of this invention to provide a method of antagonizing the functions of oxytocin in disease states in mammals. It is also a purpose of this invention to develop a method of preventing or treating the oxytocin-related disorders of preterm labor and dysmenorrhea by antagonizing the binding of oxytocin to its receptor.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. The compounds of the present invention are therefore useful in the treatment and prevention of oxytocin-related disorders of animals, preferably mammals and especially humans. These disorders are primarily preterm labor and dysmenorrhea. The compounds are also useful for stoppage of labor preparatory to cesarean delivery.

SUMMARY OF THE INVENTION

The compounds of the present invention are of the formula

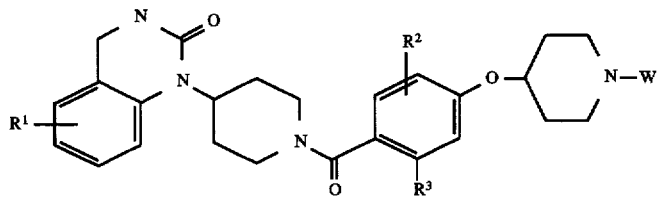

wherein W is selected from

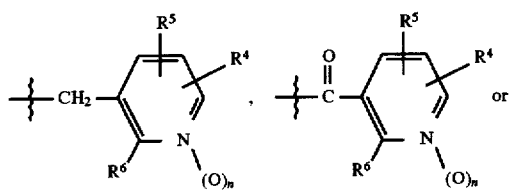

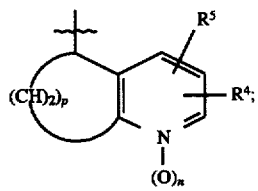

$R^1$ and $R^2$ are each independently selected from hydrogen or halogen;

$R^3$ is selected from hydrogen or $C_{1-6}$ alkoxy;

$R^4$, $R^5$ and $R^6$ are each independently selected from hydrogen, $C_{1-6}$ alkyl or halogenated $C_{1-6}$ alkyl;

n is an integer from 0 to 1; and p is an integer from 2 to 4;

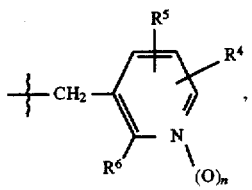

$R^3$ is selected from hydrogen or $C_{1-4}$ alkoxy;

$R^4$, $R^5$ and $R^6$ are each independently selected from hydrogen, $C_{1-4}$ alkyl or halogenated $C_{1-4}$ alkyl;

provided that at least one of $R^4$, $R^5$ and $R^6$ is halogenated $C_{1-4}$ alkyl; where all other variables are as defined above; and the pharmaceutically acceptable salts thereof.

In a class of this first embodiment is the compound wherein $R^1$ and $R^2$ are each independently selected from hydrogen or fluorine;

$R^3$ is $C_{1-4}$ alkoxy; and $R^4$, $R^5$ and $R^6$ are each independently selected from hydrogen, $C_{1-4}$ alkyl or trifluoromethyl;

provided that at least one of $R^4$, $R^5$ and $R^6$ is trifluoromethyl; where all other variables are as defined above; and the pharmaceutically acceptable salts thereof.

In a subclass of this first embodiment is the compound selected from

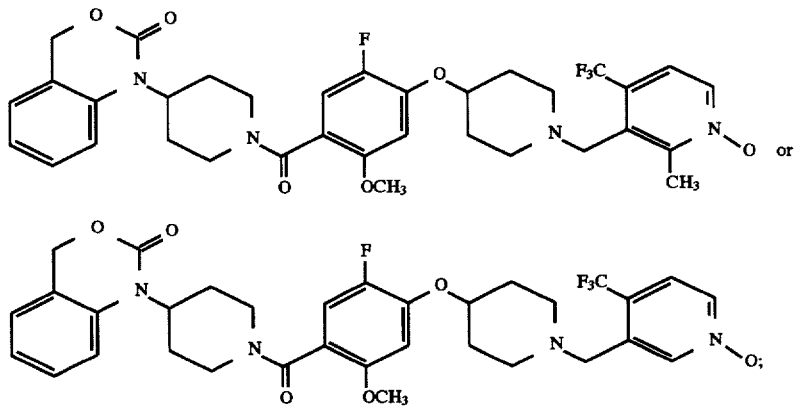

and the pharmaceutically acceptable salts thereof.

In a second embodiment of the invention is the compound wherein W is

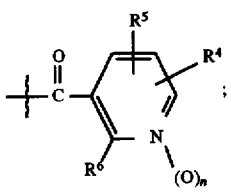

$R^3$ is selected from hydrogen or $C_{1-4}$ alkoxy;

$R^4$, $R^5$ and $R^6$ are each independently selected from hydrogen, $C_{1-4}$ alkyl or halogenated $C_{1-4}$ alkyl;

provided that when W is

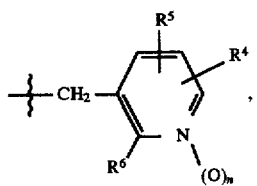

then at least one of $R^4$, $R^5$ and $R^6$ is halogenated $C_{1-6}$ alkyl; and the pharmaceutically acceptable salts thereof.

In one embodiment of the present invention is the compound wherein W is where all other variables are as defined above; and the pharmaceutically acceptable salts thereof. Preferably, in this second embodiment, when W is

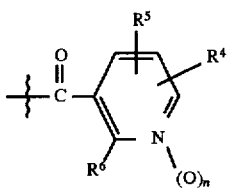

and n is zero, then $R^4$, $R^5$ and $R^6$ are not simultaneously hydrogen.

In a class of this second embodiment is the compound wherein $R^1$ and $R^2$ are each independently selected from hydrogen or fluorine;

$R^3$ is $C_{1-4}$ alkoxy; and $R^4$, $R^5$ and $R^6$ are each independently selected from hydrogen, $C_{1-4}$ alkyl or trifluoromethyl;

where all other variables are as defined above; and the pharmaceutically acceptable salts thereof.

In a third embodiment of the invention is the compound wherein W is

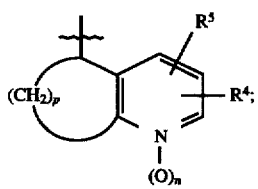

$R^3$ is selected from hydrogen or $C_{1-4}$ alkoxy;

$R^4$ and $R^5$ are each independently selected from hydrogen, $C_{1-4}$ alkyl or halogenated $C_{1-4}$ alkyl;

where all other variables are as defined above; and the pharmaceutically acceptable salts thereof.

In a class of this third embodiment is the compound wherein $R^1$ and $R^2$ are each independently selected from hydrogen or fluorine;

$R^3$ is $C_{1-4}$ alkoxy; and $R^4$ and $R^5$ are each independently selected from hydrogen, $C_{1-4}$ alkyl or trifluoromethyl;

where all other variables are as defined above; and the pharmaceutically acceptable salts thereof.

In a subclass of this third embodiment is the compound wherein W is selected from

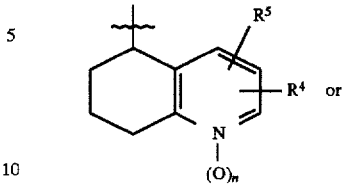

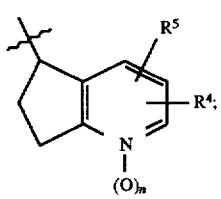

where all other variables are as defined above;

and the pharmaceutically acceptable salts thereof.

Illustrative of this third embodiment is the compound of the formula

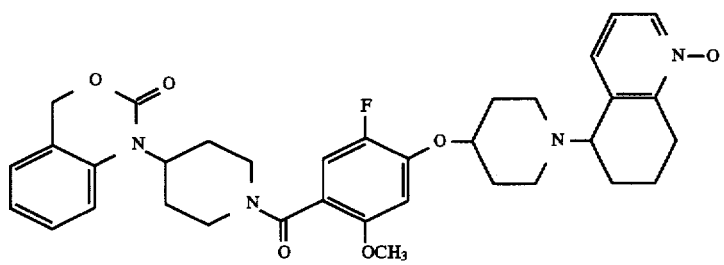

and the pharmaceutically acceptable salts thereof.

An illustration of the invention is a pharmaceutical composition comprising a pharmaceutically acceptable carrier and a therapeutically effective amount of any of the compounds described above.

Further illustrating the invention is a method of eliciting an oxytocin antagonizing effect in a mammal in need thereof, comprising administering to the mammal a therapeutically effective amount of any of the compounds or pharmaceutical compositions described above to elicit an oxytocin antagonizing effect.

An example of the invention are methods of treating preterm labor, preventing preterm labor, stopping preterm labor, stopping labor preparatory to cesarian delivery, and/or treating dysmenorrhea in a mammal in need thereof, comprising administering to the mammal a therapeutically effective amount of any of the compounds or pharmaceutical compositions described above.

Further exemplifying the invention is the use of any of the compounds described above in the preparation of a medicament for the treatment of preterm labor, dysmenorrhea and/or stoppage of labor prior to cesarian delivery in a mammal in need thereof.

More particularly illustrating the invention is a drug which is useful for treating preterm labor, dysmenorrhea and/or stopping labor prior to cesarian delivery in a mammal in need thereof, the effective ingredient of the said drug being any of the compounds described above.

More specifically exemplifying the invention are methods of increasing fertility and embryonic survival in a farm animal in need thereof, and/or controlling the timing of estrus in a farm animal in need thereof, comprising administering to the farm animal a therapeutically effective amount of any of the compounds or pharmaceutical compositions described above.

Another example of the invention is a method for improving survival of a farm animal neonate comprising controlling timing of parturition to effect delivery of the neonate during daylight hours by administering to a farm animal which is expected to deliver the neonate within 24 hours a therapeutically effective amount of any of the compounds or pharmaceutical compositions described above.

Additional illustrations of the instant invention are methods of antagonizing vasopressin from binding to its receptor site, inducing vasodilation, treating hypertension, inducing diuresis and/or inhibiting platelet agglutination in a mammal in need thereof comprising the step of administering to the mammal a therapeutically effective amount of any of the compounds or pharmaceutical compositions described above.

DETAILED DESCRIPTION OF THE INVENTION

Representative compounds of the present invention are oxytocin antagonists which display submicromolar affinity for the human oxytocin receptor. Preferred compounds of this invention were found to have $IC_{50}$ values for the human oxytocin receptor in the range of 1 nM to 50 nM.

The compounds of the present invention are administered in dosages effective to antagonize the oxytocin receptor where such treatment is needed, as in the treatment of preterm labor. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which is not specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range (i.e., methyl, ethyl, 1-propyl, 2-propyl, n-butyl, sec-butyl, tert-butyl, etc.).

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "halogen" shall include iodine, bromine, chlorine and fluorine.

The term "halogenated $C_{1-4}$ alkyl," as used herein, includes both straight and branched chain $C_{1-4}$ alkanes wherein one or more of the hydrogen atoms on the alkyl chain is replaced with a halogen atom (e.g., $CF_3$).

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and dysmenorrhea. These compounds may also find usefulness for stoppage of labor preparatory to cesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

The present invention is also directed to combinations of the compounds of the present invention with one or more agents useful in the treatment of disorders such as preterm labor, dysmenorrhea and stopping labor prior to cesarean delivery. More specifically, the compounds of the instant invention may be effectively administered in combination with effective amounts of other tocolytic agents used in the treatment of preterm labor such as β-adrenergic agonists (e.g., ritodrine, isoproterenol, terbutaline, albuterol), magnesium sulfate, ethanol, other oxytocin antagonists (e.g., atosiban), calcium transport blockers (e.g., nicardipine, nifedipine), prostaglandin synthesis inhibitors (e.g., indomethacin), nitric oxide donors (e.g., nitroglycerine, S-nitroso-N-acetylpenicillamine), phosphodiesterase inhibitors, and progestins (e.g., progesterone). Preferred combinations are simultaneous or alternating treatments of an oxytocin receptor antagonist of the present invention and a second tocolytic agent. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. The compounds of the instant invention may also be used in combination with antenatal steroids (e.g., dexamethasone). This particular combination has beneficial effects on the neonate by both decreasing uterine activity to prolong gestation and increasing fetal maturation. It will be understood that the scope of combinations of the compounds of this invention with other agents useful for treating oxytocin related conditions includes in principle any combination with any pharmaceutical composition useful for treating preterm labor, dysmenorrhea or stopping labor prior to cesarean delivery.

The oxytocin antagonist compounds of the present invention are also useful for improving reproductive efficiency in farm animals. In certain farm animals (e.g., sheep, cattle, swine, horses and goats), the beginning of the estrous cycle is typically marked by behavioral estrus when the female animal accepts the male for mating. Ovulation of the ovarian follicle occurs shortly after onset of estrus and cells in the follicle give rise to the corpus luteum. The cells that form the corpus luteum produce progesterone and they also produce oxytocin. The secretion of oxytocin from the corpus luteum and/or pituitary acts on the uterine endometrium to stimulate the secretion of prostaglandins (in particular PGF) which, in turn, causes the regression of the corpus luteum of the ovary. PGF is, therefore, the luteolytic hormone. In the cycling animal (i.e., where mating and fertilization have not occurred), destruction of the corpus luteum removes the source of progesterone which is key to the preparation of the uterus for pregnancy. The presence of a viable conceptus (i.e., the embryo and its associated membranes) is necessary to prevent the luteolytic process. In fact, the first key signal that the conceptus must produce is the one to prevent regression of the corpus luteum (i.e., the maternal recognition of pregnancy signal). Thus, in the animal where mating and fertilization have occurred, the conceptus secretes a factor that antagonizes the action of oxytocin to induce luteolysis. This results in maintenance of a functioning corpus luteum and the continued secretion of progesterone which is obligatory to the initiation of pregnancy.

Administration of an oxytocin antagonist of the present invention at this critical period after fertilization (i.e., just prior to or during the period of maternal recognition of pregnancy) supplements the natural signal from the conceptus (i.e., maternal recognition of pregnancy) to prolong corpus luteal function. The result is to increase pregnancy rates by enhancing the chances of impregnation through a reduction in embryonic loss. Thus, to improve fertility and embryonic survival in a farm animal, a mated animal, for example, a mated ewe, is treated with an oxytocin antagonist compound beginning on between day 10 to day 15 after onset of estrus. The oxytocin antagonist compound is administered to the mated animal for a period of one day to three weeks, preferably one week to three weeks, most preferably one week to two weeks.

The compounds of the present invention are also useful for controlling the timing of parturition in farm animals so that delivery of the neonates occurs during the daytime. Approximately 80% of livestock are delivered at night and up to 5 to 10% of newborns die because the deliveries are not monitored properly. An oxytocin antagonist compound of the present invention administered to the mother on the evening before expected delivery delays parturition so that the delivery occurs during the daylight hours. By delaying the timing of parturition, proper monitoring of the delivery and the neonates is ensured, resulting in increased survival rates of the newborns.

In addition, the oxytocin antagonists of the instant invention can also be used to control the timing of estrus in a cycling farm animal by preventing luteal regression. An oxytocin antagonist compound of the instant invention is administered to a cycling farm animal prior to expected estrus to prevent regression of the corpus luteum. Daily administration of the compound retards estrus until administration of the compound ceases. Preferably, the oxytocin antagonist compound is administered at least 1 day prior to expected estrus. By delaying estrus in a group of farm animals, a farmer can synchronize estrus among the group to provide time and cost savings in farm management.

The compounds of the present invention also bind to the vasopressin receptor and are therefore useful as vasopressin antagonists. Vasopressin antagonists are useful in the treatment or prevention of disease states involving vasopressin disorders; thus, the compounds are useful for inducing vasodilation, treating hypertension, inducing diuresis, inhibiting platelet agglutination and treating congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.0025 to 5.0 gm/day orally. More particularly, when administered orally for the treatment of preterm labor, an effective daily dose will be in the range of 0.005 mg/kg to about 100 mg/kg of body weight, preferably, from 0.1 mg/kg to 50 mg/kg, most preferably from 0.1 mg/kg to 50 mg/kg, administered in single or divided dose. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethyl-aspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Abbreviations used in the instant specification, particularly the Schemes and Examples, are as follows:

Bn = benzyl
Boc = t-butyloxycarbonyl
BOP = benzotriazol-1-yloxytris(dimethylamino) phosphonium hexafluorophosphate
DCC = 1,3-dicyclohexylcarbodiimide
DCM = dichloromethane
DEAD = diethyl azodicarboxylate
DIEA = diisopropylethylamine
DMAP = 4-dimethylaminopyridine
DMF = dimethylformamide
DMSO = dimethyl sulfoxide
Et = ethyl
EtOAc = ethyl acetate
EtOH = ethanol
EDC = 1-ethyl-3-(3-dimethylaminopropyl)carbodiimide
FAB MS = fast atom bombardment mass spectroscopy
HOAc = acetic acid
HOBT or HBT = 1-hydroxybenzotriazole
HPLC = high performance liquid chromatography
IPA = isopropyl acetate
LAH = lithium aluminum hydride
LDA = lithium diisopropylamide
m-CPBA or MCPBA = meta-chloroperoxybenzoic acid
Me = methyl
MeOH = methanol
MOM = methoxymethyl
MTBE = methyl tert-butyl ether
NCS = N-chlorosuccinimide
NMR = nuclear magnetic resonance
Ph = phenyl
PPTS = pyridinium p-toluenesulfonate
t-Bu = tert-butyl
TFA = trifluoroacetic acid
THF = tetrahydrofuran
TLC = thin layer chromatography
TMEDA = N, N, N', N'-tetramethylethylenediamine
TMS = trimethylsilyl
TMS-allyl = allyltrimethylsilane The compounds of the present invention can be prepared readily according to the following examples, or modifications thereof, using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in the following Examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds.

Dry THF was obtained by distillation from calcium hydride under inert atmosphere. Dry DMF and dry $CH_2Cl_2$ were obtained by storing the reagent grade solvents over 3Å molecular sieves. Determination of reaction pH was estimated by spotting an aliquot from the reaction mixture on wetted E. Merck "colorpHast" pH 1–14 indicator strips. Silica coated TLC plates were used to monitor all reactions (Analtech Uniplate, 2.4×10 cm, Silica Gel GF, 250 micron thickness). Pressurized silica gel column chromatography using 230–400 mesh silica gel was performed according to the method of Still, Kahn, and Mitra, *J. Org. Chem.*, 1978, vol. 43, p. 2923. All temperatures are degrees Celsius. $^1$H NMR spectra were measured at 300 MHz on a Varian XL-300, at 400 MHz on a Varian XL-400, using $(CH_3)_4Si$ as an internal standard All NMR spectra for the compounds of the Examples which follow were consistent with the assigned structures. Fast atom bombardment mass spectra were obtained on a VG-ZAB-HF spectrometer. Analytical HPLC were run on a Spectra Physics SP4270/8800 instrument using the following conditions:

Column: Vydac $C_{18}$, 0.21×15 cm UV detection at 215 nm

| Mobile Phases | A = 0.1% by volume TFA in $H_2O$<br>B = 0.1% by volume TFA in acetonitrile<br>C = 0.1% by volume $H_3PO_4$ in water<br>D = acetonitrile |
|---|---|
| Method A: | |
| Gradient | T = 0 min, 95% A, 5% B<br>T = 15 min, 0% A, 100% B |
| Flow = 2.0 mL/min | |
| Method B: | |
| Gradient | T = 0 min, 95% A, 5% B<br>T = 30 min, 5% A, 95% B |
| Flow = 1.5 mL/min | |
| Method C: | |
| Gradient | T = 0 min, 95% C, 5% D<br>T = 15 min, 5% C, 95% D |
| Flow = 1.5 mL/min | |

EXAMPLE 1

1-(1-(4-(4-Piperidinyloxy)-2-methoxybenzoyl)piperidin-4-yl)-4(H)-3,1-benzoxazin-2(1H)-one

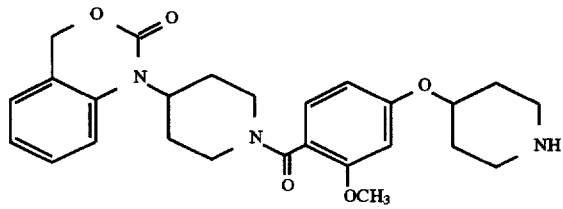

Step 1. 1-t-Butyloxycarbonyl-4-piperidinone (20 g, 0.10 mol), 2-aminobenzyl alcohol (13 g, 0.11 mol), and acetic acid (14 mL, 0.22 mol) were dissolved in dry toluene (500 mL). The solution was refluxed under inert atmosphere for 3 h with azeotropic removal of water. The solution was cooled to ambient temperature and concentrated under reduced pressure to one half of the original volume. To the solution was added $NaBH_3CN$ (20 g, 0.32 mol) and dry THF (300 mL). Acetic acid (10 mL, 0.15 mmol) was added dropwise over a period of about 1 h. The reaction was stirred at ambient temperature for 24 h. The mixture was concentrated under reduced pressure and the residue was dissolved in EtOAc (750 mL). The EtOAc layer was washed with saturated aqueous $NaHCO_3$ (3×500 mL) and brine (250 mL). The EtOAc layer was dried ($MgSO_4$), filtered, and the solvent was removed under reduced pressure. The residue was purified by pressurized silica gel column chromatography, using a gradient elution of 15–30% EtOAc-hexanes. 1-t-Butyloxycarbonyl-4-((2-hydroxymethyl)phenylamino)-piperidine was obtained as a gum (TLC: $R_f$= 0.30 (30:70 EtOAc:hexanes); HPLC (method A) retention time= 8.89 min).

Step 2. 1-t-Butyloxycarbonyl-4-((2-hydroxymethyl)-phenylamino)piperidine (24 g, 78 mmol) from step 1 above was dissolved in dry THF (250 mL) and cooled to 0° C. under an atmosphere of nitrogen. To the solution was added DIEA (41 mL, 0.24 mol) and triphosgene (8.54 g, 28.8 mmol). The reaction was stirred at 0° C. for 1 h, and then at ambient temperature for 24 h. Ether (250 mL) was added, the mixture was cooled to 0° C. and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous $NaHCO_3$ (2×500 mL). The EtOAc layer was dried ($MgSO_4$), filtered, and the solvent was removed under reduced pressure. The residue was boiled in ether (ca. 200 mL) until the solid had dissolved. Cooling overnight gave 1-(N-t-butyloxy-carbonyl-4-piperidinyl)-4H-3,1-benzoxazin-2(1H)-one as off-white crystals, mp 143°–145° C. (TLC: $R_f$= 0.28 (30:70 EtOAc:hexanes); HPLC (method A) retention time= 8.77 min; FAB MS: m/z 333 ($M^+$+H)).

Step 3. A stirred solution of 1-(N-t-butyloxycarbonyl-4-piperidinyl)-4H-3,1-benzoxazin-2(1H)-one (19 g, 57 mmol) from step 2 above in EtOAc (500 mL) was cooled to 0° C. HCl gas was bubbled through the solution for 30 min. Stirring was continued at 0° C. for 1 h, during which time a precipitate had formed, and the reaction was warmed to ambient temperature for 1 h. The stirred suspension was cooled to 0° C. and cold ether (250 mL) was added. The precipitate was collected by filtration and washed with ether. The solid was dried under reduced pressure for 18 h, giving 1-(4-piperidinyl)-4H-3,1-benzoxazin-2(1H)-one hydrochloride as a white amorphous solid (TLC: $R_f$= 0.29 (90:10:1 $CH_2Cl_2$:MeOH:$NH_4OH$); HPLC (method A) retention time= 3.88 min; FAB MS: m/z 233 ($M^+$+H)).

Step 4: To a stirred solution of triphenylphosphine (57.2 g, 0.218 mol) and methyl 2,4-dihydroxybenzoate (29.2 g, 0.174 mol) in dry THF (250 mL) at 0° C. was added a solution of N-t-butyloxy-4-piperidinol (43.8 g, 0.218 mol) and diethyl azodicarboxylate (37.9 mL, 0.218 mol) in dry THF (150 mL) dropwise over a period of 2 h. The resulting solution was warmed to ambient temperature over 2 h and stirred for an additional 16 h. The solvent was concentrated to half of the original volume under reduced pressure, ether (200 mL) was added, and the mixture was cooled to 0° C. for 3 h. The precipitated triphenylphosphine oxide was removed by filtration and washed with cold ether, and the filtrate solvents were removed under reduced pressure. The residue was purified by pressurized silica gel column chromatography using a gradient elution of 10–25% EtOAc-hexane. Methyl 4-(N-t-butoxycarbonyl-4-piperidinyloxy)-2-hydroxybenzoate was obtained as a waxy solid.

Step 5: To a solution of methyl 4-(N-t-butoxycarbonyl-4-piperidinyloxy)-2-hydroxybenzoate (50 g, 0.14 mol) from Step 4 above and iodomethane (17.4 mL, 0.28 mol) in DMF (300 mL) at 0° C. was added NaH (6.55 g of a 60% suspension in mineral oil, 0.164 mol) in several portions over a period of 2 h. The resulting suspension was warmed to ambient temperature and stirred for 18 h. The mixture was quenched with methanol (5 mL) and concentrated under reduced pressure. The residue was suspended in EtOAc (500 mL) and washed with water (2×250 mL) and brine (250 mL). The EtOAc layer was dried (MgSO₄), filtered, and concentrated under reduced pressure. The crude product was purified by pressurized silica gel column chromatography using a gradient elution of 20–40% EtOAc-hexane. Methyl 4-(N-t-butoxycarbonyl-4-piperidinyloxy)-2-methoxybenzoate was obtained as a gum that solidified on standing (TLC: R_f= 0.25 (3:1 hexane:EtOAc); HPLC (method A) retention time= 9.72 min).

Step 6: Methyl 4-(N-t-butoxycarbonyl-4-piperidinyloxy)-2-methoxybenzoate (35 g, 96 mmol) from Step 5 above was dissolved in MeOH (250 mL) and to the solution was added 2 N NaOH (100 ML, 200 mmol). The stirred mixture was warmed to 70° C. for 3 h. The solution was cooled to ambient temperature, concentrated under reduced pressure, cooled to 0° C. and 0.5M aqueous citric acid solution (300 mL) was added. To the suspension was added EtOAc (500 mL) and water (300 mL). The EtOAc layer was separated and the aqueous phase was washed with EtOAc (200 mL). The combined EtOAc layers were washed with brine (250 mL), dried (MgSO₄), filtered, and the solvent was removed under reduced pressure to give 4-(N-t-butoxycarbonyl-4-piperidinyloxy)-2-methoxybenzoic acid as a foam that solidified on standing in vacuo (HPLC (method A) retention time= 8.46 min).

Step 7: 4-(N-t-Butoxycarbonyl-4-piperidinyloxy)-2-methoxybenzoic acid from step 6 above (4.6 g, 13 mmol), the hydrochloride salt of 1-(4-piperidinyl)-4(H)-3,1-benzoxazin-2(1H)-one from step 3 above (3.5 g, 13 mmol), HOBT (2.5 g, 16 mmol), and EDC (4.9 g, 17 mmol) were combined and dissolved in DMF (100 mL). To the stirred solution was added DIEA (4.5 mL, 26 mmol) until the reaction was pH 7 as judged by spotting an aliquot on wetted E. Merck "colorpHast" pH 1–14 indicator strips. The reaction was stirred at ambient temperature for 18 h and the solvent was removed under reduced pressure. The residue was dissolved in EtOAc (150 mL) and washed with 5% aqueous citric acid (75 mL), water (50 mL), and saturated aqueous NaHCO₃ (75 mL). The EtOAc layer was dried (MgSO₄), filtered, and the solvent was removed under reduced pressure. The residue was purified by pressurized silica gel column chromatography using a gradient elution of 1–4% MeOH-DCM. The title compound was obtained as a white foam by evaporation of a DCM solution under reduced pressure (TLC R_f= 0.15 (98:2 DCM:MeOH); HPLC (method A) retention time 10.06 min; FAB MS: m/z 566 (M⁺+H)).

Step 8: 1-(1-(4-(N-t-Butoxycarbonyl-4-piperidinyloxy)-2-methoxybenzoyl) piperidin-4-yl)-4(H)-3,1-benzoxazin-2(1H)-one from step 7 above (5.0 g, 8.8 mmol) was dissolved in EtOAc (100 mL) and cooled to 0° C. HCl gas was bubbled through the stirred solution for 20 min, and the mixture was warmed to ambient tempertare and stirred for 30 min. Excess HCl was removed by bubbling argon through the solution for 15 min. Ether (150 mL) was added and the mixture was cooled to 0° C. for 30 min. The precipitate was collected by filtration and was dried in vacuo for 24 h to give the hydrochloride salt of the title compound as an amorphous solid. A small portion of this material was purified to greater than 99% homogeneity by preparative reverse phase HPLC using an acetonitrile-water gradient containing 0.1% TFA. The TFA salt of the title compound was obtained as an amorphous solid by lyophilization.

Analysis calculated for (C₂₆H₃₁N₃O₅, 1.35 TFA, 0.25 H₂O) C, 55.24; H, 5.31; N, 6.73; Found C, 55.27; H, 5.29; N, 6.70; TLC: R_f= 0.33 (90:10:0.5 DCM:MeOH:NH₄OH); HPLC (method A): retention time 6.14 min; FAB MS: m/z 466 (M⁺+H)

EXAMPLE 2
1-(1-(4-(4-piperidinyloxy)-5-fluoro-2-methoxybenzoyl) piperidin-4-yl)-4H-3, 1-benzoxazin-2(1H)-one

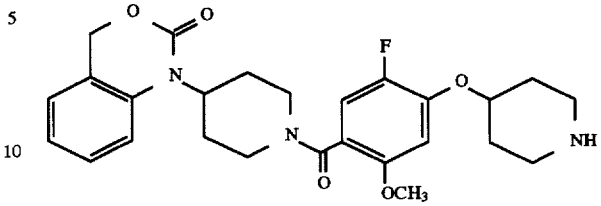

Step 1. To a well-stirred, 0° C. solution of methyl 2,4-dihydroxybenzoate (50 g, 300 mmol) in acetone (1000 mL) was added K₂CO₃ (150 g, 1000 mmol) and benzyl bromide (39 mL, 330 mmol). The solution was allowed to warm to ambient temperature over 48 h. The mixture was filtered through celite and the filtrate solvent was removed under reduced pressure. The residue was dissolved in EtOAc (1000 mL) and washed with water (250 mL) and saturated aqueous NaHCO₃ (500 mL). The EtOAc layer was dried (MgSO₄), filtered, and the EtOAc was removed under reduced pressure. The residue was purified by pressurized silica gel column chromatography using 5:1 hexanes:EtOAc as eluant. Methyl 4-benzyloxy-2-hydroxybenzoate was obtained as a white powder.

Step 2. To a stirred, 0° C. solution of methyl 4-benzyloxy-2-hydroxybenzoate (12g, 46 mmol) from step 1 above in DMF (150 mL) was added NaH (2.76 g of a 60% suspension in mineral oil, 69 mmol) and methyl iodide (7.2 mL, 116 mmol). The solution was warmed to ambient temperature and stirred for 18 h. The reaction mixture was poured onto ice and the resulting solution was extracted with ether (3×200 mL). The organic phase was dried (MgSO₄), filtered and the solvent was removed under reduced pressure. The residue was purified by pressurized silica gel column chromatography using 4:1 hexanes:EtOAc as eluant. Methyl 4-benzyloxy-2-methoxybenzoate was obtained as a white powder.

Step 3. A round-bottomed flask containing methyl 4-benzyloxy-2-methoxybenzoate (16.48 g, 60 mmol) from step 2 above was purged with argon and 10% palladium on carbon catalyst was added (2 g). Methanol (200 mL) was slowly added followed by HOAc (2 mL). The solution was kept under 1 atm of H₂ and stirred for 24 h. The catalyst was removed by filtration through celite and the filtrate solvents were removed under reduced pressure. The residue was purified by pressurized silica gel column chromatography using 1:1 hexanes:EtOAc as eluant. Methyl 4-hydroxy-2-methoxybenzoate was obtained as an amorphous solid.

Step 4. Methyl 4-hydroxy-2-methoxybenzoate (10 g, 55 mmol) from step 3 above and 1-fluoro-3,5-dichloropyridinium trifluoromethanesulfonate (21 g, 66 mmol) were refluxed in dichloromethane (250 mL) for 48 h. The solution was washed with 5% aqueous citric acid (250 mL) and the organic phase was dried (MgSO₄), filtered, and the solvent was removed under reduced pressure. The residue was purified by pressurized silica gel column chromatography using 99:1 CH₂Cl₂:MeOH as eluant. Crystallization from ether gave methyl 5-fluoro-4-hydroxy-2-methoxybenzoate.

Step 5. Methyl 5-fluoro-4-hydroxy-2-methoxybenzoate from step 4 above was coupled to N-Boc-4-piperidinol using Mitsunobu conditions as given in step 4 of Example 1. Methyl 4-(N-t-butyloxycarbonyl-4-piperidinyloxy)-5-fluoro-2-methoxybenzoate was obtained as a gum (TLC R_f=

0.19 (3:7 EtOAc:hexanes); HPLC (method A) retention time= 9.9 min).

Step 6. Methyl 4-(N-t-butyloxycarbonyl-4-piperidinyloxy)-5-fluoro-2-methoxybenzoate from step 5 above was saponified using the procedure given in step 6 of Example 1. 4-(N-t-butyloxycarbonyl-4-piperidinyloxy)-5-fluoro-2-methoxybenzoic acid was obtained as an amorphous solid (HPLC (method A) retention time= 8.6 min).

Step 7. 4-(N-t-butyloxycarbonyl-4-piperidinyloxy)-5-fluoro-2-methoxybenzoic acid from step 6 above and 1-(4-piperidinyl)-4H-3,1-benzoxazin-2(1H)-one hydrochloride from step 3 of Example 1 were coupled using the procedure given in step 6 of Example 1. 1-(1-(4-(N-tert-butyloxycarbonyl-4-piperidinyloxy)-5-fluoro-2-methoxybenzoyl) piperidin-4-yl)-4H-3,1-benzoxazin-2(1H)-one was obtained as an amorphous solid (TLC $R_f$= 0.17 (4:1 EtOAc:hexanes); HPLC (method A) retention time= 9.8 min); FAB MS m/z 584 (M$^+$+H)).

Step 8. The title compound was prepared from 1-(1-(4-(N-t-butyloxycarbonyl-4-piperidinyloxy)-5-fluoro-2-methoxybenzoyl)-piperidin-4-yl)-4H-3,1 -benzoxazin-2(1H)-one from step 7 above using the procedure given in step 3 of Example 1. The hydrochloride salt of 1-(1-(4-(4-piperidinyloxy)-5-fluoro-2-methoxybenzoyl)piperidin-4-yl)-4H-3,1-benzoxazin-2(1H)-one was obtained as an amorphous solid.

Analysis calculated for $C_{26}H_{30}FN_3O_5$, 2.0 HCl, 0.15 EtOAc C, 56.08; H, 5.87; N, 7.38; Found C, 56.02; H, 5.94; N, 7.37; TLC: $R_f$= 0.12 (96:4:0.4 $CH_2Cl_2$:MeOH:NH$_4$OH); HPLC(method A) retention time= 6.2 min; FAB MS m/z 484 (M$^+$+H)

EXAMPLE 3

1-(1-(4-(1-(N-oxo-2-methyl-3-pyridylmethyl)-4-piperidinyloxy)-2-methoxybenzoyl) piperidin-4-yl)-4(H)-3,1 -benzoxazin-2(1H)-one Step 1. To a stirred solution of ethyl 2-methylnicotinate (1.50 g, 9.09 mmol) in THF (65 mL) at 0° C. was added LAH (9.1 mL of a 1.0 M solution in THF; 9.1 mmol). The mixture was stirred at ambient temperature for 18 h and then quenched by the sequential addition of ethyl acetate (0.1 mL), water (0.1 mL), 15% aqueous NaOH (0.1 mL) and water (0.28 mL). The solids were removed by filtration through celite and the filtrate solvents were removed under reduced pressure. 3-Hydroxymethyl-2-methylpyridine was obtained as an oil (TLC: $R_f$= 0.40 (5:95 MeOH:$CH_2Cl_2$)).

Step 2. To a stirred solution of 3-hydroxymethyl-2-methylpyridine (1.00 g, 8.13 mmol) from step 1 above in $CH_2Cl_2$ (40 mL) at ambient temperature was added SOCl$_2$ (9.5 g, 80 mmol). The mixture was stirred for 4 h, and the solvent and excess SOCl$_2$ were evaporated under reduced pressure. The residue was partitioned between $CH_2Cl_2$ (50 mL) and saturated aqueous NaHCO$_3$ (100 mL). The organic layer was separated, and the aqueous layer was washed with additional $CH_2Cl_2$ (2×40 mL). The combined organic layers were evaporated under reduced pressure to give 3-chloromethyl-2-methyl-pyridine as a solid which was used in the next step without purification (TLC: $R_f$= 0.85 (95:5 $CH_2Cl_2$:MeOH); FAB MS m/z 142 (M$^+$+H)).

Step 3. To a stirred solution of 3-chloromethyl-2-methylpyridine (0.50 g, 3.5 mmol) from step 2 above in CHCl$_3$ (40 mL) was added MCPBA (1.1 g of 50% MCPBA by weight; 3.5 mmol). After 1.5 h, the solution was extracted with saturated aqueous NaHCO$_3$ (40 mL), water (40 mL), dried (MgSO$_4$), filtered, and evaporated under reduced pressure. The residue was purified by pressurized silica gel column chromatography using 97:3 $CH_2Cl_2$:MeOH as eluant. 3-Chloromethyl-2-methylpyridine-N-oxide was obtained as a solid (TLC: $R_f$= 0.30 (97:3 $CH_2Cl_2$:MeOH); FAB MS m/z 158 (M$^+$+H)).

Step 4: To a stirred solution of 1-(1-(4-(4-piperidinyloxy)-2-methoxybenzoyl) piperidin-4-yl)-4(H)-3,1-benzoxazin-2 (1H)-one from Example 1 (6.24 g, 13.4 mmol) in DMF (150 mL) under argon atmosphere was added 3-chloromethyl-2-methylpyridine-N-oxide from step 3 above (2.33 g, 14.8 mmol) and DIEA (3.5 mL, 20 nimol). The reaction mixture was stirred at ambient temperature for 48 hours. The solvent was removed under reduced pressure. The residue was partitioned between saturated aqueous NaHCO$_3$ (100 mL) and $CH_2Cl_2$ (100 mL). The organic phase was dried (MgSO$_4$), filtered, and the solvent was removed under reduced pressure. The residue was purified by pressurized silica gel column chromatography using 97:3:0.3 $CH_2Cl_2$:MeOH:NH$_4$OH as eluant to give the title compound. To a solution of the title compound (500 mg) in MeOH (10 mL) was added 1.1 equivalents of aqueous HCl and the solvent was removed under reduced pressure. The residue was dissolved in 5:1 $H_2O$:$CH_3CN$ and lyophilized to give a white solid. The amorphous HCl salt (500 mg) was dissolved in hot isopropanol (8 mL). Cooling to ambient temperature gave a crystalline mono-hydrochloride, monohydrate salt of the title compound.

Analysis calculated for $C_{33}H_{38}N_4O_6$, 1.0 HCl, 1.0 $H_2O$ C, 61.81; H, 6.45; N, 8.74; Found C, 61.54; H, 6.32; N, 8.60; TLC: $R_f$= 0.30 (95:5:0.5 $CH_2Cl_2$:MeOH:NH$_4$OH); HPLC (method A) retention time= 5.84 min; FAB MS m/z 587 (M$^+$+H);

EXAMPLE 4

1-(1-(4-(1-(N-oxo-4-trifluoromethyl-3-pyridylmethyl)-4-piperidinyloxy)-2-methoxybenzoyl) piperidin-4-yl)-4(H)-3,1-benzoxazin-2(1H)-one

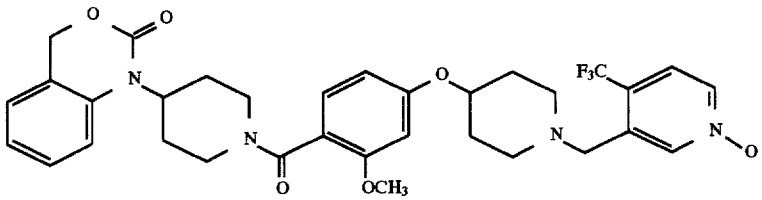

Step 1. To a stirred suspension of LAH (0.64 g, 17.0 mmol) in THF (30 mL) at −78° C. was added dropwise methyl 4-trifluoromethylnicotinate (1.74 g, 8.48 mmol) in THF (20 mL). The mixture was stirred for 1 h then carefully quenched with aqueous NaHCO$_3$ (80 mL) and extracted with CH$_2$Cl$_2$ (3×100 mL). The combined organic extracts were dried (Na$_2$SO$_4$) and concentrated in vacuo to give 3-hydroxymethyl-4-trifluoromethylpyridine as an oil (TLC: R$_f$= 0.35 (1:1 hexane:EtOAc)).

Step 2. To a stirred solution of 3-hydroxymethyl-4-trifluoromethylpyridine (1.11 g, 6.27 mmol) from step 1 above in CH$_2$Cl$_2$ (20 mL) at 0° C. was added SOCl$_2$ (0.89 g, 7.5 nmuol) in CH$_2$Cl$_2$ (10 mL). The mixture was allowed to warm to room temperature and stirred for 1 h, and the solvent and excess SOCl$_2$ were evaporated under reduced pressure. The residue was concentrated from cyclohexane (3−) to give 3-chloromethyl-4-trifluoromethylpyridine hydrochloride as a solid which was used in the next step without purification (TLC: R$_f$= 0.75 (1:1 hexane:EtOAc)).

Step 3. 3-Chloromethyl-4-trifluoromethylpyridine hydrochloride (204 mg, 0.88 mmol) from step 2 above was dissolved in CHCl$_3$ (50 mL) and treated with saturated aqueous NaHCO$_3$. The organic layer was removed, dried (Na$_2$SO$_4$), and concentrated to give the free pyridine. This 3-chloromethyl-4-(trifluoromethyl)pyridine was dissolved in CHCl$_3$ (10 mL) and MCPBA was added (0.19 g of 80% MCPBA by weight; 0.88 mmol). After 29 h, the solution was extracted with saturated aqueous NaHCO$_3$ (10 mL), dried (Na$_2$SO$_4$), filtered, and evaporated under reduced pressure. The residue was purified by pressurized silica gel column chromatography eluting with EtOAc. 3-Chloromethyl-4-trifluoromethylpyridine-N-oxide was obtained as a solid (TLC: R$_f$= 0.35 (EtOAc); FAB MS m/z 212 (M$^+$+H)).

Step 4: To a stirred solution of 1-(1-(4-(4-piperidinyloxy)-2-methoxybenzoyl) piperidin-4-yl)-4(H)-3,1-benzoxazin-2 (1H)-one hydrochloride from Example 1 (0.274 g, 0.546 mmol) in DMF (2 mL) under argon atmosphere was added 3-chloromethyl-4-trifluoromethylpyridine-N-oxide from step 3 above (0.105 g, 0.496 mmol) and DIEA (0.225 mL, 1.29 mmol). The reaction mixture was stirred at ambient temperature for 96 hours. The solvent was removed under reduced pressure. The residue was partitioned between saturated aqueous NaHCO$_3$ (10 mL) and EtOAc (20 mL). The organic phase was dried (Na$_2$SO$_4$), filtered, and the solvent was removed under reduced pressure. The residue was purified by pressurized silica gel column chromatography eluting with a gradient of 99:1:0.5 to 97:3:0.5 CH$_2$Cl$_2$:MeOH:NH$_4$OH to give the title compound. To a solution of the title compound in EtOH was added 1 equivalent of 12 N HCl and the solvent was removed under reduced pressure. The residue was triturated with Et$_2$O to give a colorless solid, the monohydrochloride salt of the title compound.

Analysis calculated for C$_{33}$H$_{35}$F$_3$N$_4$O$_6$, 1.0 HCl, 1.1 H$_2$O, 0.95 EtOH C, 56.59; H, 5.97; N, 7.56; Found C, 56.60; H, 5.76; N, 7.51; TLC: R$_f$= 0.50 (95:5:1 CHCl$_3$:MeOH:NH$_4$OH); HPLC (method C) retention time= 7.7 min; FAB MS m/z 641 (M$^+$+H)

EXAMPLE 5

1-(1-(4-(1-(4-trifluoromethyl-3-pyridylmethyl)-4-piperidinyloxy)-2-methoxybenzoyl) piperidin-4-yl)-4(H)-3,1-benzoxazin-2(1H)-one

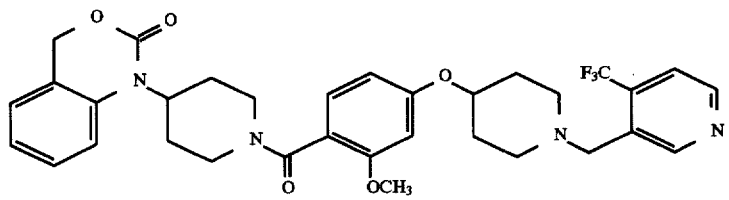

To a stirred solution of 1-(1-(4-(4-pipefidinyloxy)-2-methoxybenzoyl)-piperidin-4-yl)-4(H)-3,1-benzoxazin-2 (1H)-one hydrochloride from Example 1 (0.238 g, 0.474 mmol) in DMF (2 mL) under argon atmosphere was added 3-chloromethyl-4-trifluoromethylpyridine hydrochloride from step 2 of Example 4 (0.100 g, 0.431 mmol) and DIEA (0.27 mL, 1.55 mmol). The reaction mixture was stirred at ambient temperature for 96 hours. The solvent was removed under reduced pressure. The residue was partitioned between saturated aqueous NaHCO$_3$ (10 mL) and EtOAc (20 mTL). The organic phase was dried (Na$_2$SO$_4$), filtered, and the solvent was removed under reduced pressure. The residue was purified by pressurized silica gel column chromatography eluting with a gradient of 99:1:0.5 to 97:3:0.5 CH$_2$Cl$_2$:MeOH:NH$_4$OH to give the title compound. To a solution of the title compound in EtOH was added 1 equivalent of 12 N HCl and the solvent was removed under reduced pressure. The residue was triturated with Et$_2$O to give a colorless solid, the monohydrochloride salt of the title compound.

Analysis calculated for C$_{33}$H$_{35}$F$_3$N$_4$O$_5$, 1.0 HCl, 1.25 H$_2$O C, 57.98; H, 5.68; N, 8.20; Found C, 57.99; H, 5.69; N, 8.26; TLC: R$_f$= 0.35 (97:3:1 CHCl$_3$:MeOH:NH$_4$OH); HPLC (method C) retention time= 8.1 min

EXAMPLE 6

1-(1-(4-(1-(N-oxo-2-methyl-4-trifluoromethyl-3-pyridylmethyl)-4-piperidinyloxy)-5-fluoro-2-methoxybenzoyl)piperidin-4-yl)-4(H)-3,1-benzoxazin-2 (1H)-one

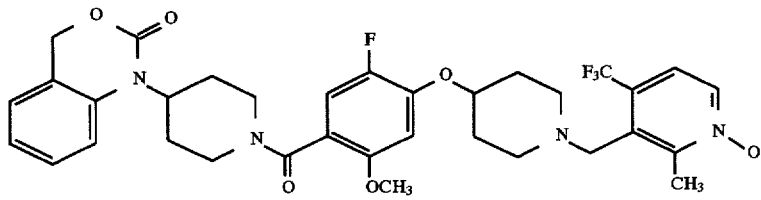

Step 1. Methyl 2-methyl-4-trifluoromethylnicotinate was reduced using the procedure as given in step 1 of Example 3. 3-Hydroxymethyl-2-methyl-4-trifluoromethylpyridine was obtained as a pale yellow waxy solid(TLC $R_f$= 0.31 (97:3 $CH_2Cl_2$:MeOH)).

Step 2. 3-Hydroxymethyl-2-methyl-4-trifluoromethylpyridine from step 1 above was converted to the chloride using the procedure given in step 2 of Example 3. The crude 3-chloromethyl-2-methyl-4-trifluoromethylpyridine was purified by pressurized silica gel column chromatography using 95:5 hexane:EtOAc as eluant. 3-Chloromethyl-2-methyl-4-trifluoromethylpyridine was obtained as a white solid (TLC $R_f$= 0.45 (9:1 hexane:EtOAc)).

Step 3. 3-Chloromethyl-2-methyl-4-trifluoromethyl- pyridine from step 2 above was oxidized using the procedure as given in step 3 of Example 3. 3-Chloromethyl-2-methyl-4-trifluoromethyl-pyridine-N-oxide was obtained as a white solid (TLC $R_f$= 0.21 (97:3 $CH_2Cl_2$:MeOH)).

Step 4. 3-Chloromethyl-2-methyl-4-trifluoromethyl-pyridine-N-oxide from step 3 above was used to alkylate 1-(1-(4-(4-piperidinyloxy)-5-fluoro-2-methoxybenzoyl) piperidin-4-yl)-4H-3,1 -benzoxazin-2(1H)-one from Example 2 using conditions as given in step 4 of Example 3. The crude product was purified by pressurized silica gel column chromatography using 98:2:0.2 $CH_2Cl_2$:MeOH:$NH_4OH$ as eluant to give the title compound. The hydrochloride salt of 1-(1-(4-( 1-(N-oxo-2-methyl-4-trifluoromethyl-3-pyridylmethyl)-4-piperidinyloxy)-5-fluoro-2-methoxybenzoyl) piperidin-4-yl)-4(H)-3,1 -benzoxazin-2(1H)-one was obtained as an amorphous solid.

Analysis calculated for $C_{34}H_{36}F_4N_4O_6$, 0.65 HCl, 0.9 $H_2O$ C, 57.30; H, 5.44; N, 7.86; Found C, 57.32; H, 5.44; N, 7.66; TLC: $R_f$= 0.15 (98:2:0.2 $CH_2Cl_2$:MeOH:$NH_4OH$); HPLC (method A) retention time= 6.85 min FAB MS m/z673 ($M^+$+H)

EXAMPLE 7

1-(1-(4-(1-(2-methyl-4-trifluoromethyl-3-pyridylmethyl)-4-piperidinyloxy)-5-fluoro-2-methoxybenzoyl)piperidin-4-yl)-4(H)-3,1-5 benzoxazin-2(1H)-one

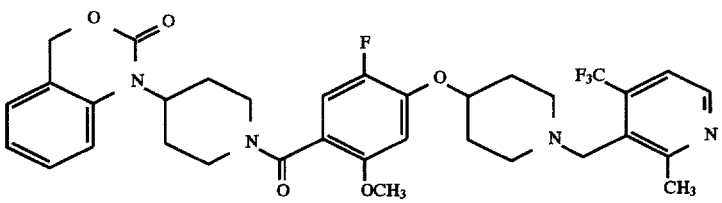

3-Chloromethyl-2-methyl-4-trifluoromethylpyridine from step 2 of Example 6 was used to alkylate 1-(1-(4-(4-piperidinyloxy)-5-fluoro-2-methoxybenzoyl) piperidin-4-yl)-4H-3,1-benzoxazin-2(1H)-one from Example 2 using conditions as given in step 4 of Example 3. The crude product was purified by pressurized silica gel column chromatography using 98:2:0.2 $CH_2Cl_2$:MeOH:$NH_4OH$ as eluant and then by preparative reverse phase HPLC using an acetonitrile-water gradient containing 0.1% TFA. The TFA salt of 1-(1-(4-(1-(N-oxo-2-methyl-4-trifluoromethyl-3-pyridylmethyl)-4-piperidinyloxy)-5-fluoro-2-methoxybenzoyl)piperidin-4-yl)-4(H)-3,1-benzoxazin-2 (1H)-one was obtained as an amorphous solid by lyophilization.

Analysis calculated for $C_{34}H_{36}F_4N_4O_5$, 1.85 TFA, 0.35 $H_2O$ C, 51.81; H, 4.45; N, 6.41; Found C, 51.81; H, 4.47; N, 6.43; TLC: $R_f$= 0.27 (98:2:0.2 $CH_2Cl_2$:MeOH:$NH_4OH$); HPLC (method A) retention time= 7.75 min; FAB MS m/z 657 ($M^+$+H)

EXAMPLE 8

1-(1-(4-(1-(N-oxo-2-methyl-4-trifluoromethyl-3-pyridylmethyl)-4-piperidinyloxy)-2-methoxybenzoyl)piperidin-4-yl)-4(H)-3,1-benzoxazin-2(1H)-one

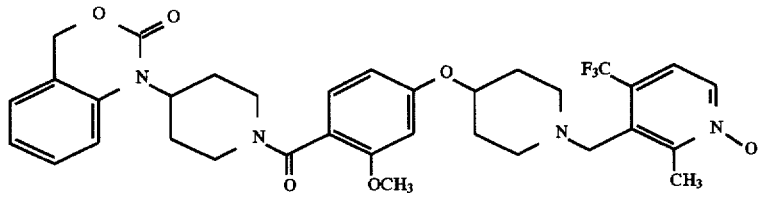

3-Chloromethyl-2-methyl-4-trifluoromethylpyridine-N-oxide from step 3 of Example 6 was used to alkylate 1-(1-(4-(4-piperidinyloxy)-2-methoxybenzoyl)piperidin-4-yl)-4H-3,1-benzoxazin-2(1H)-one from Example 1 using conditions as given in step 4 of Example 3. The crude product was purified by pressurized silica gel column chromatography using 98:2:0.2 $CH_2Cl_2$:MeOH:$NH_4OH$ as eluant to give the title compound. The hydrochloride salt of 1-(1-(4-(1-(N-oxo-2-methyl-4-trifluoromethyl-3-pyridylmethyl)-4-piperidinyloxy)-2-methoxybenzoyl)piperidin-4-yl)-4(H)-3,1-benzoxazin-2(1H)-one was obtained as an amorphous solid.

Analysis calculated for $C_{34}H_{37}F_3N_4O_6$, 0.45 HCl, 0.85 $H_2O$ C, 59.49; H, 5.75; N, 8.16; Found C, 59.47; H, 5.75; N, 8.13; TLC: $R_f$= 0.12 (98:2:0.2 $CH_2Cl_2$:MeOH:$NH_4OH$); HPLC (method A) retention time= 6.65 min; FAB MS m/z 655 ($M^+$+H)

EXAMPLE 9

1-(1-(4-(1-(2-methyl-4-trifluoromethyl-3-pyridylmethyl)-4-piperidinyloxy)-2-methoxybenzoyl)piperidin-4-yl)-4(H)-3,1-benzoxazin-2(1H)-one

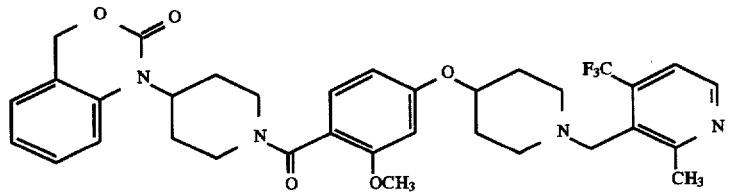

3-Chloromethyl-2-methyl-4-trifluoromethylpyridine from step 2 of Example 6 was used to alkylate 1-(1-(4-(4-piperidinyloxy)-2-methoxybenzoyl)piperidin-4-yl)-4H-3,1-benzoxazin-2(1H)-one from Example 1 using conditions as given in step 4 of Example 3. The crude product was purified by pressurized silica gel column chromatography using 98:2:0.2 $CH_2Cl_2$: MeOH:$NH_4OH$ as eluant and then by preparative reverse phase HPLC using an acetonitrile-water gradient containing 0.1% TFA. The TFA salt of 1-(1-(4-(1-(N-oxo-2-methyl-4-trifluoromethyl-3-pyridylmethyl)-4-piperidinyloxy)-2-methoxybenzoyl)piperidin-4-yl)-4(H)-3,1-benzoxazin-2(1H)-one was obtained as an amorphous solid by lyophilization.

Analysis calculated for $C_{34}H_{37}F_3N_4O_5$, 1.75 TFA, 0.55 $H_2O$ C, 53.10; H, 4.74; N, 6.61; Found C, 53.1 1; H, 4.74; N, 6.58; TLC: $R_f$= 0.24 (98:2:0.2 $CH_2Cl_2$:MeOH:$NH_4OH$); HPLC (method A) retention time= 7.58 min; FAB MS m/z 639 ($M^+$+H)

EXAMPLE 10

1-(1-(4-(1-(N-oxo-5,6,7,8-tetrahydroquinolin-5-(R,S)-yl)-4-piperidinyloxy)-5-fluoro-2-methoxybenzoyl)piperidin-4-yl)-4(H)-3,1-benzoxazin-2(1H)-one

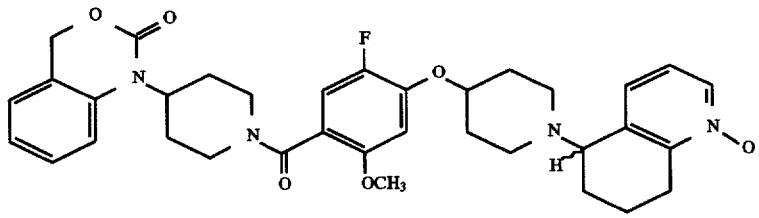

Step 1. 5,6,7,8-Tetrahydro-5-quinolinone, synthesized according to the literature procedure by F. Zymalkowski and H. Rimek, *Arch. Pharm.* (1961) volume 294, pp. 759–765, (10.0 g, 67.9 mol) was dissolved in MeOH (350 mL) and cooled to 0° C. under an atmosphere of nitrogen. To the solution was added NaBH₄ (7.7 g, 0.204 mol) portionwise over 60 minutes. The reaction was stirred at ambient temperature for 24 h. The mixture was concentrated under reduced pressure and partitioned between EtOAc (600 mL) and saturated aqueous NaHCO₃ (250 mL). The EtOAc layer was dried (MgSO₄), filtered, and the solvent was removed under reduced presssure. The residue was purified by pressurized silica gel column chromatography using 97:3 CH₂Cl₂:MeOH as eluant. 5-Hydroxy 5,6,7,8-tetrahydroquinoline was obtained as a pale yellow solid (TLC R$_f$= 0.14 (98:2 CH₂Cl₂:MeOH)).

Step 2. 5-Hydroxy-5,6,7,8-tetrahydroquinoline from step 1 above was converted to the chloride using the procedure as given in step 2 of Example 3. The crude 5-chloro-5,6,7,8-tetrahydroquinoline was purified by pressurized silica gel column chromatography using 7:3 EtOAc:hexane as eluant. 5-Chloro-5,6,7,8-tetrahydroquinoline was obtained as a pale yellow oil (TLC R$_f$= 0.40 (8:2 EtOAc:hexane)).

Step 3. 5-Chloro-5,6,7,8-tetrahydroquinoline from step 2 above was oxidized using the procedure as given in step 3 of Example 3. 5-Chloro 5,6,7,8-tetrahydroquinoline-N-oxide was obtained as a white solid (TLC R$_f$= 0.24 (97:3 CH₂Cl₂: MeOH)).

Step 4. To a stirred solution of 1-(1-(4-(4-piperidinyloxy)-5-fluoro-2-methoxybenzoyl)piperidin-4-yl)-4H-3,1-benzoxazin-2(1H)-one from Example 2 (0.45 g, 0.93 mmol) in DMF (5 mL) under argon atmosphere was added 5-chloro-5,6,7,8-tetrahydroquinoline-N-oxide (170 mg, 0.93 mmol) from step 3 above, NaI (279 mg, 1.86 mmol), and DIEA (0.34 mL, 1.86 mmol). The reaction mixture was stirred at 40° C. for 48 hours. The solvent was removed under reduced pressure. The residue was partitioned between saturated aqueous NaHCO₃ (10 mL) and CH₂Cl₂ (10 mL). The organic phase was dried (MgSO₄), filtered, and the solvent was removed under reduced pressure. The residue was purified by pressurized silica gel column chromatography using 97:3:0.3 CH₂Cl₂:MeOH:NH₄OH as eluant to give the title compound. The compound was further purified by preparative reverse phase HPLC using an acetonitrile-water gradient containing 0.1% TFA. The pure fractions were collected and evaporated to give a concentrated aqueous solution of the product. The solution was added to saturated aqueous NaHCO₃ (30 mL) and extracted with CH₂Cl₂ (2×15 mL). The organic layer was dried (MgSO₄), filtered and evaporated under reduced pressure to give a white solid. To a solution of the title compound (210 mg) in MeOH (5 mL) was added 1.1 equivalents of aqueous HCl and the solvent was removed under reduced pressure. The HCl salt of the title compound was obtained as an amorphous solid after lyophilization from 5:1 water-acetonitrile.

Analysis calculated for C₃₅H₃₉FN₄O₆, 1.05 HCl, 1.55 H₂O C, 60.31; H, 6.24; N, 8.04; Found C, 60.32; H, 6.25; N, 8.20; TLC: R$_f$= 0.30 (97:3:0.3 CH₂Cl₂: MeOH:NH₄OH); HPLC (method A) retention time= 6.02 min; FAB MS m/z 632 (M⁺+H)

EXAMPLE 11

(−)-1-(1-(4-(1-(N-oxo-5,6,7,8-tetrahydroquinolin-5-yl)-4-piperidinyloxy)-5-fluoro-2-methoxybenzoyl)piperidin-4-yl)-4(H)-3,1-benzoxazin-2(1H)-one

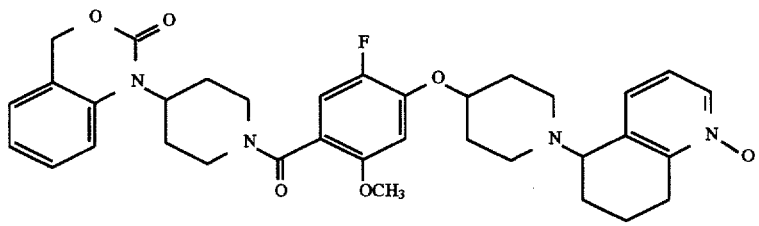

A sample of racemic 1-(1-(4-(1-(N-oxo-5,6,7,8-tetrahydroquinolin-5-(R,S)-yl)-4-piperidinyloxy)-5-fluoro-2-methoxybenzoyl)piperidin-4-yl)-4(H)-3,1-benzoxazin-2 (1H)-one (13 mg) from Example 10 was resolved by preparative chiral HPLC using a ChiralPak AD column (2 cm×25cm) eluting with a mobile phase consisting of 50:25:25:0.1 hexane:MeOH:EtOH:TFA and a flow rate of 6.0 mL/min. The retention time of the first eluting fraction using this method was 31.7 minutes. The fractions containing the first eluting isomer were evaporated and lyophilized from 5:1 water-acetonitrile to give the TFA salt of the title compound as an amorphous solid.

Analysis calculated for C₃₅H₃₉FN₄O₆, 2.0 TFA, 0.45 H₂O C, 54.03; H, 4.87; N, 6.46; Found C, 54.45; H, 5.09; N, 6.07; TLC: R$_f$= 0.30 (97:3:0.3 CH₂Cl₂:MeOH:NH₄OH); FAB MS m/z632(M⁺+H)

[α]$_D^{20}$=−33° C.

EXAMPLE 12

(+)-1-(1-(4-(1-(N-oxo-5,6,7,9-tetrahydroquinolin-5-yl)-4-piperidinyloxy)-5-fluoro-2-methoxybenzoyl)piperidin-4-yl)-4(H)-3,1-benzoxazin-2(1H)-one

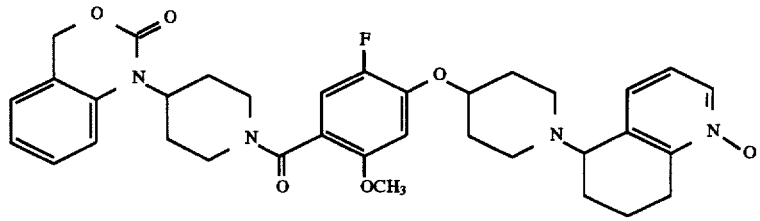

A sample of racemic 1-(1-(4-(1-(N-oxo-5,6,7,9-tetrahydroquinolin-5-(R,S)-yl)-4-piperidinyloxy)-5-fluoro-2-methoxybenzoyl)piperidin-4-yl)-4(H)-3,1-benzoxazin-2

(1H)-one (13 mg) from Example 10 above was resolved using the procedure given in Example 11. The retention time of the second eluting fraction using this method was 40.4 minutes. The fractions containing the second eluting isomer were evaporated and lyophilized from 5:1 water-acetonitrile to give the TFA salt of the title compound as an amorphous solid.

Analysis calculated for $C_{35}H_{39}FN_4O_6$. 1.7 TFA, 0.1 $H_2O$ C, 55.81; H, 4.99; N, 6.78; Found C, 55.82; H, 4.89; N, 6.07; TLC: $R_f$= 0.30 (97:3:0.3 $CH_2Cl_2$: MeOH:$NH_4OH$); FAB MS m/z 632 ($M^+$+H)

$[\alpha]_D^{20}$=+31° C.

EXAMPLE 13

1-(1-(4-(1-(5,6,7,8-tetrahydroquinolin-5-(R,S)-yl)-4-piperidinyloxy)-5-fluoro-2-methoxybenzoyl)piperidin-4-yl)-4(H)-3,1-benzoxazin-(1H)-one Analysis calculated for $C_{35}H_{39}FN_4O_5$. 1.0 HCl, 0.45 $H_2O$ C, 67.50; H, 6.46; N, 9.00; Found C, 67.49; H, 6.51; N, 8.94; TLC: $R_f$= 0.25 (94:6 EtOAc:MeOH); HPLC (method C) retention time= 6.6 min; FAB MS m/z 615 ($M^+$+H)

EXAMPLE 14

1-(1-(4-(1-(N-oxo-4-trifluoromethyl-3-pyridylmethyl)-4-piperidinyloxy)-5-fluoro-2-methoxybenzoyl)piperidin-4-yl)-4(H)-3,1-benzoxazin-2(1H)-one

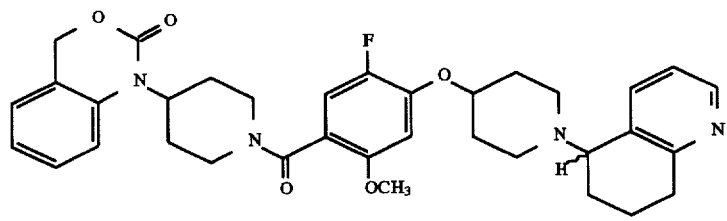

To a stirred solution of 1-(1-(4-(4-piperidinyloxy)-5-fluoro-2-methoxybenzoyl)piperidin-4-yl)-4H-3,1-

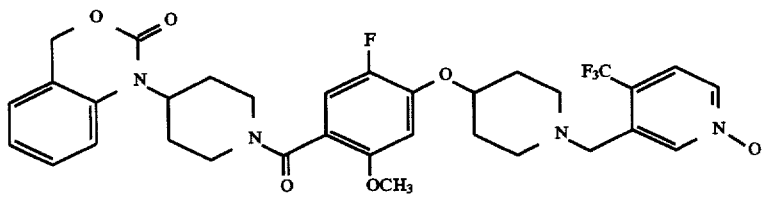

benzoxazin-2(1H)-one hydrochloride from Example 2 (0.744 g, 1.43 mmol) in DMF (8 mL) under argon atmosphere was added 5-chloro-5,6,7,8-tetrahydro-quinoline (0.216 g, 1.29 mmol) from step 2 of Example 10, NaI (214 mg, 1.43 mmol), and DIEA (0.55 mL, 3.16 mmol). The reaction mixture was stirred at 40° C. for 72 hours. The solvent was removed under reduced pressure. The residue was partitioned between saturated aqueous $NaHCO_3$ (50 mL) and EtOAc (100 mL). The organic layer was removed and the aqueous layer was extracted with EtOAc (2×50 mL). The combined organic extracts were dried ($Na_2SO_4$), filtered, and the solvent was removed under reduced pressure. The residue was purified by pressurized silica gel column chromatography eluting with a gradient of 98:2 to 94:6 EtOAc:MeOH to give the title compound. The hydrochloride salt of the title compound was obtained as a colorless solid.

1-(1-(4-(4-Piperidinyloxy)-5-fluoro-2-methoxybenzoyl)-piperidin-4-yl)-4H-3,1-benzoxazin-2(1H)-one from Example 2 was alkylated with 2-chloromethyl-4-trifluoromethylpyridine-N-oxide from step 3 of Example 4 using the procedure given in step 4 of Example 4. The crude product was purified by pressurized silica gel column chromatography using a gradient elution of 97:3:0.3 to 95:5:0.5 $CH_2Cl_2$:MeOH:$NH_4OH$. The hydrochloride salt of the title compound was obtained as an amorphous solid by lyophilization from acetonitrile:water containing aqueous HCl.

Analysis calculated for $C_{33}H_{34}F_4N_4O_6$, 0.95 HCl, 0.9 $H_2O$ C, 56.00; H, 5.21; N, 7.92; Found C, 56.00; H, 5.21; N, 7.78; TLC: $R_f$= 0.16 (97:3:0.3 $CH_2Cl_2$:MeOH:$NH_4OH$); HPLC (method A) retention time= 6.8 min; FAB MS m/z 659 ($M^+$+H)

EXAMPLE 15

1-(1-(4-(1-(4-trifluoromethyl-3-pyridylmethyl)-4-piperidinyloxy)-5-fluoro-2-methoxybenzoyl)piperidin-4-yl)-4(H)-3,1-benzoxazin-2(1H)-one

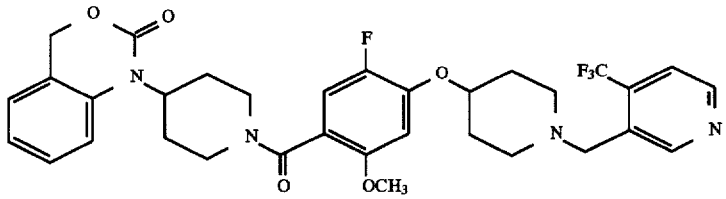

1-(1-(4-(4-Piperidinyloxy)-5-fluoro-2-methoxybenzoyl)-piperidin-4-yl)-4H-3,1-benzoxazin-2(1H)-one from Example 2 was alkylated with 2-chloromethyl-4-trifluoromethylpyridine from step 2 of Example 4 using the procedure given in Example 5. The crude product was purified by pressurized silica gel column chromatography using 97:3:0.3 $CH_2Cl_2$:MeOH:$NH_4OH$ as eluant. The hydrochloride salt of the title compound was obtained as an amorphous solid by lyophilization from acetonitrile:water containing aqueous HCl.

Analysis calculated for $C_{33}H_{34}F_4N_4O_5$, 1.55 HCl, 0.5 $H_2O$ C, 55.96; H, 5.20; N, 7.91; Found C, 55.93; H, 5.20; N, 7.53; TLC: $R_f$= 0.31 (97:3:0.3 $CH_2Cl_2$:MeOH:$NH_4OH$); HPLC (method A) retention time= 7.26 min; FAB MS m/z 642 ($M^+$+H)

EXAMPLE 16

1-(1-(4-(1-(2-methyl-3-pyridylcarbonyl)-4-piperidinyloxy)-2-methoxybenzoyl)piperidin-4-yl)-4(H)-3,1-benzoxazin-2(1H)-one

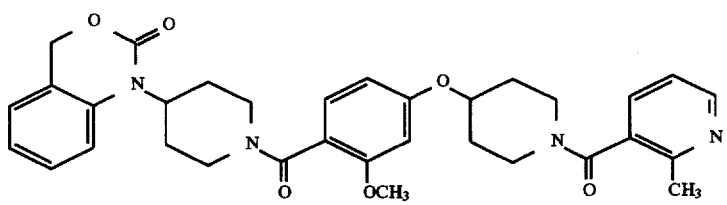

1-(1-(4-(4-Piperidinyloxy)-2-methoxybenzoyl)piperidin-4-yl)-4H-3,1-benzoxazin-2(1H)-one from Example 1 and 2-methylnicotinic acid were coupled using the procedure given in step 7 of Example 1. The crude product was purified by pressurized silica gel column chromatography using a gradient elution of 1–3% MeOH in $CH_2Cl_2$. The hydrochloride salt of the title compound was obtained as an amorphous solid by lyophilization from acetonitrile-water containing aqueous HCl.

Analysis calculated for $C_{33}H_{36}N_4O_6$, 0.85 HCl, 0.4 $H_2O$ C, 63.63; H, 6.09; N, 9.00; Found C, 63.63; H, 6.10; N, 9.09; TLC: $R_f$= 0.32 (97:3 $CH_2Cl_2$:MeOH); HPLC (method A) retention time= 6.47 min; FAB MS m/z 585 ($M^+$+H)

EXAMPLE 17

1-(1-(4-(1-(N-oxo-2-methyl-3-pyridylcarbonyl)-4-piperidinyloxy)-2-methoxybenzoyl)piperidin-4-yl)-4(H)-3,1-benzoxazin-2(1H)-one

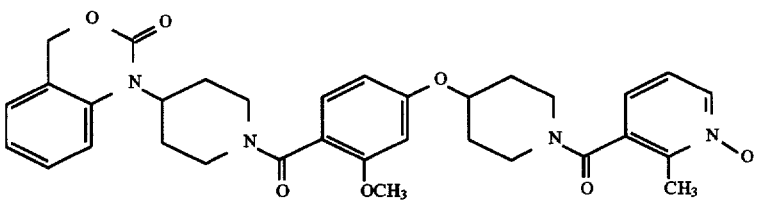

1-(1-(4-(1-(2-Methyl-3-pyridylcarbonyl)-4-piperidinyloxy)-2-methoxybenzoyl)piperidin-4-yl)-4(H)-3,1-benzoxazin-2(1H)-one from Example 14 was oxidized using the procedure given in step 3 of Example 3. The crude product was purified by pressurized silica gel column chromatography using a gradient elution of 2–4% MeOH in $CH_2Cl_2$. The hydrochloride salt of the title compound was obtained as an amorphous solid by lyophilization from acetonitrile-water containing aqueous HCl.

Analysis calculated for $C_{33}H_{36}N_4O_7$, 1.15 $H_2O$ C, 63.78; H, 6.21; N, 9.02; Found C, 63.78; H, 5.85; N, 8.99; TLC: $R_f$= 0.20 (97:3 $CH_2Cl_2$:MeOH); HPLC (method A) retention time= 6.85 min; FAB MS m/z 601 ($M^+$+H)

EXAMPLE 18

Alternate Syntheses of Intermediate 4-(N-t-butyloxycarbonyl-4-piperidinyloxy)-5-fluoro-2-methoxybenzoic acid 5.

Alternative methods for the synthesis of 4-(N-t-butyloxycarbonyl-4-piperidinyloxy)-5-fluoro-2-methoxybenzoic acid (also referred to as 5; see below), an intermediate used for the preparation of 1-(1-(4-(4-piperidinyloxy)-5-fluoro-2-methoxybenzoyl)piperidin-4-yl)-4H-3,1-benzoxazin-2(1H)-one from Example 2, are given below.

Method A: Starting from 2,4,5-trifluorobenzoate 8:

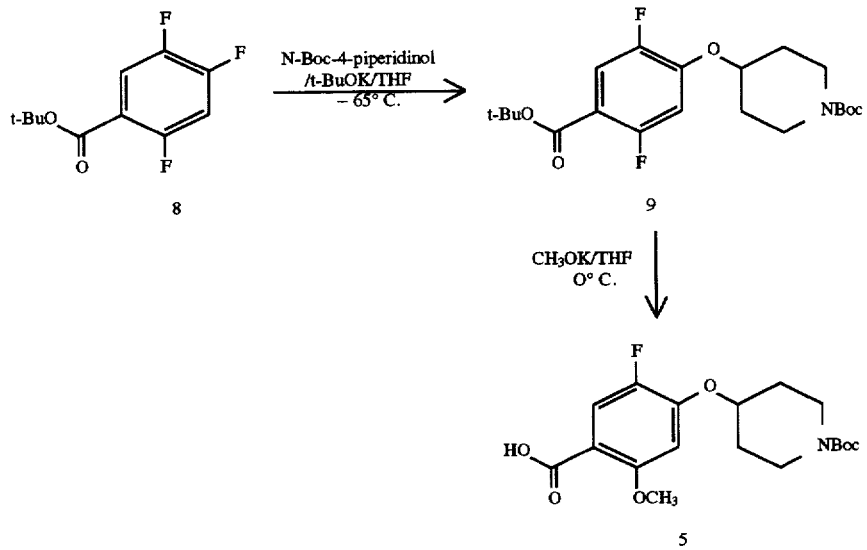

Step 1. To a solution of N-Boc-4-piperidine (1.95 g, 9.68 mmol) in THF (5.0 ml) was added a solution of t-BuOK in THF (Aldrich, 1.0 M, 10.6 ml) at 0° C. and the resulting reaction mixture was stirred for 0.5 h at that temperature. The reaction mixture was slowly cannulated to a cold solution of trifluoroester 8 (2.05 g, 8.80 mmol) in THF (5.0 ml) at −65° C. and was then aged at −30° C. for 1.5 h. The reaction was quenched with water (5.0 ml) at −30° C. and then extracted with MTBE (150 ml). The organic layer was washed with water (30 ml), then brine (30.0 ml) and dried over MgSO₄. Evaporation of the solvents gave an oily residue. Chromatography of the residue on silica gel (eluted with 5% ethyl acetate/hexane) provided product 9.

Step 2. To a solution of t-BuOK in THF (1.0 M, 2.0 ml) was added MeOH (0.081 ml, 2.0 mmol) at −4° C. and the resulting solution was stirred for 0.5 h. A THF solution of 9 (165 mg, 0.40 mmol) was introduced at −4° C. and the reaction mixture was stirred at 0° C. for 1.0 h. The reaction mixture was allowed to warm to 25° C. and stirred for 6 h. The reaction mixture was diluted with MTBE (25 ml) and water (25 ml) at 25 ° C. The aqueous layer was separated and then neutralized with 2 N HCl to pH= 1. The neutralized aqueous layer was extracted with CH₂Cl₂ (25 ml x 2). The combined organic layers were washed with water (25 ml) and dried over MgSO₄. Evaporation of the solvent gave the solid acid 5.

Method B: Starting from 2,4,5-trifluorobenzonitrile 11:

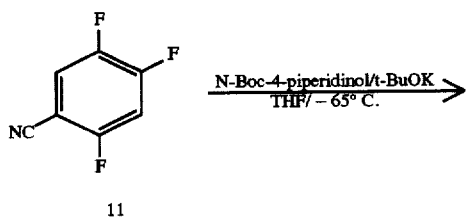

Step 1. A t-BuOK solution (1.0 M, 5.0 ml) was slowly added to a solution of N-Boc-4-piperidinol (1.0 g, 4.97 mmol) in THF (3.0 ml) at 5° C. and the resulting mixture stirred for 0.5 h. The mixture was then transferred to a cold solution of trifluoronitrile 11 (Aldrich, 0.569 ml, 4.97 mmol) in THF (3.0 ml) at −65° C. The reaction mixture was stirred at −65° C. for 3.0 h and then allowed to warm to 25° C. over 1.0 h. The reaction mixture was quenched with water (25 ml) and was diluted with MTBE (100 ml). The organic layer was separated and washed with water (35 ml), brine (35 ml), and dried over MgSO₄. Evaporation of the solvent under vacuum provided 12 as a white solid.

Step 2. MeOH (0.151 ml, 3.73 mmol) was added to a solution of t-BuOK in THF (1.0 M, 3.73 ml) at 5° C. resulting in a light suspension which was stirred for 0.5 h at 5° C. The light suspension was cannulated into a cold solution of difluoronitrile 12 (0.84 g, 2.485 mmol) in THF (3.0 ml) at -50° C. and then aged for 1.0 h at -50° C. The reaction mixture was warmed to 5° C. over 0.5 h and stirred at 5° C. for 2 h after which the reaction was quenched with water (15 ml). The reaction mixture was diluted with MTBE (100 ml), and the organic layer was washed with water (35 ml), then brine (35 ml). After drying over MgSO₄, the organic layer was evaporated to dryness to provide a waxy solid of monofluoronitrile 13.

Step 3. A NaOH solution (3.0 ml, 50 wt. %) was added to a solution of 13 (0.416 g, 1.19 mmol) in EtOH (3.0 ml), followed by addition of water (3.0 ml) at 25° C. The resulting slurry was heated to 70° C. for 16 h and then cooled to 5° C. Conc. HCl was added at 5 ° C to adjust the pH to 1, and the mixture was then extracted with ethyl acetate (100 ml). The organic layer was separated and washed with water (25 ml), brine (25 ml) and dried over MgSO₄. Evaporation of the solvent gave the acid 5 as a white solid.

EXAMPLE 19

As a specific embodiment of an oral composition, 100 mg of the compound of Example 10 is formulated with sufficient finely divided lactose to provide a total amount of 580 to 590 mg to fill a size O hard gel capsule.

EXAMPLE 20

RAT & HUMAN OT/AVP BINDING ASSAYS

The high affinity binding of [³H]oxytocin (OT) to uterine tissue and [³H]arginine vasopressin (AVP) to liver (AVP-V₁ site) and kidney (AVP-V₂ site) tissue was determined using crude membrane preparations as described previously [Pettibone, D. J., et al., *J. Pharmacol. and Exper. Ther.*, 256(1): 304–308 (1991)]. Uterine tissue was taken from nonpregnant adult Sprague-Dawley rats (Taconic Farms, Germantown, N.Y.) pretreated (18–24 h) with diethylstilbestrol propionate (DES; 300 µg/kg, i.p.). Uterine tissue (full thickness) was also taken with informed consent from nonlabor pregnant women undergoing cesarean section at 38 to 39 weeks gestation (Oregon Health Sciences Center, Portland, Oreg.). Liver and kidney medulla samples were taken from male rats and from human surgical and early postmortem donors (National Disease Research Interchange, Philadelphia PA; Analytical Biological Services, Wilmington, DE).

Competition studies were conducted at equilibrium using 1 nM [³H]OT or 0.5 nM [³H]AVP in the following buffer: 50 mM Tris, 5 mM MgCl₂, 0.1% bovine serum albumin. Nonspecific binding was determined using 1 µM unlabeled OT or AVP in their respective assays. The binding reactions were initiated by the addition of tissue preparation and terminated by filtration using a Skatron cell harvester (model 7019, Skatron, Inc., Sterling, Va.). Ki values were calculated for each compound using three to six separate IC₅₀ determinations ($K_i = IC_{50}/[1-c/K_d]$); [Cheng, Y-C; Prusoff, W. H.; *Biochem. Pharmacol.* 22:3099 (1973)] with mean $K_d$ values obtained from replicate (n=3) equilibrium saturation binding assays (10 point, 100 fold concentration range): [³H]OT rat uterus, 0.69 nM; human myometrium, 1.1 nM; [³H]AVP: rat liver, 0.21 nM; rat kidney, 0.27 nM; human liver, 0.27 nM; human kidney, 1.4 nM. Computer analysis of the saturation assays by EBDA/LIGAND [McPherson, G. A.: Kinetic, Ebda, Ligand, Lowry: A Collection of Radioligand Binding Analysis Programs, Elsevier Science Publishers, Amsterdam (1985)] indicated that both radioligands apparently bound to single sites in all tissues examined. The final protein concentration for the various tissues in each assay ranged from 150 to 300 µg/ml [Lowry, P. H.; Rosebrough, N. J.; Farr, A. L.; Randall, R. J.; *J. Biol. Chem.*, 193:265–275 (1951)].

IC₅₀ values were determined for the [³H]OT and [³H]AVP binding assays by linear regression of the relation log concentration of compound vs. percent inhibition of specific binding. Data is either reported as a given percentage of inhibition at a specified concentration, or if an IC₅₀ was calculated, as a nanomolar concentration. Representative compounds of the present invention were found to have IC₅₀ values for oxytocin in the range of 1 nM to 50 nM.

The oxytocin antagonistic effect of the compounds of the present invention can be further evaluated according to the in vitro and/or in vivo functional assays described in detail in D. J. Pettibone et al., *Drug Devel. Res.* 1993, 30, 129–142.

While the foregoing specification teaches the principles of the present invention, with examples for the purpose of illustration, it will be understood that the practice of the invention encompasses all of the usual variations, adaptions and/or modifications as come within the scope of the following claims and their equivalents.

What is claimed is:

1. A compound of the formula

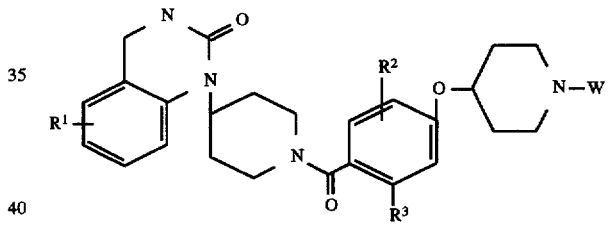

wherein W is selected from

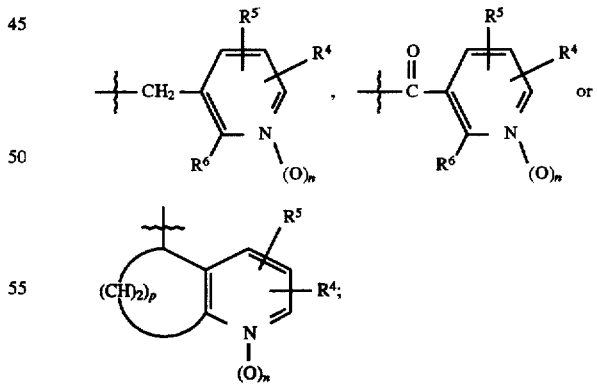

R¹ and R² are each independently selected from halogen;
R³ is selected from hydrogen or C₁₋₆ alkoxy;
R⁴, R⁵ and R⁶ are each independently selected from hydrogen, straight chain C₁₋₆ alkyl or trifuormethyl;
n is an integer from 0 to 1; and
p is 3 or 4;

provided that when W is

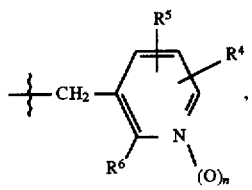

then at least one of R⁴, R⁵ and R⁶ is trifluoromethyl; or a pharmaceutically acceptable salt thereof.

2. The compound of claim 1, wherein W is

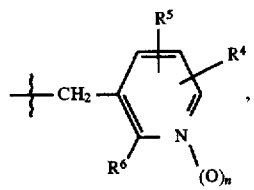

$R^3$ is selected from hydrogen or $C_{1-4}$ alkoxy;

$R^4$, $R^5$ and $R^6$ are each inependently selected from hydrogen, straight chain $C_{1-4}$ alkyl or trifluoromethyl;

provided that at least one of $R^4$, $R^5$ and $R^6$ is trifluoromethyl;

or a pharmaceutically acceptable salt thereof.

3. The compound of claim 2, wherein $R^1$ and $R^2$ are each independently selected from hydrogen or fluorine;

$R^3$ is $C_{1-4}$ alkoxy; and $R^4$, $R^5$ and $R^6$ are each independently selected from hydrogen, straight chain $C_{1-4}$ alkyl of trifluoromethyl;

provided that at least one of $R^4$, $R^5$ and $R^6$ is trifluoromethyl;

or a pharmaceutically acceptable salt thereof.

4. A compound which is:

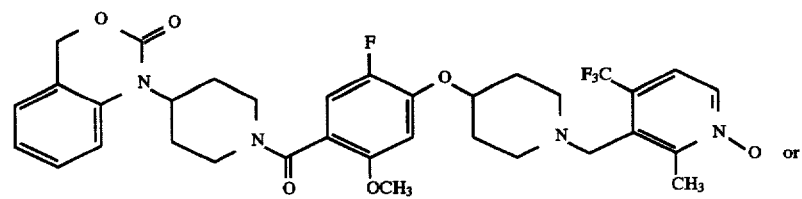

or

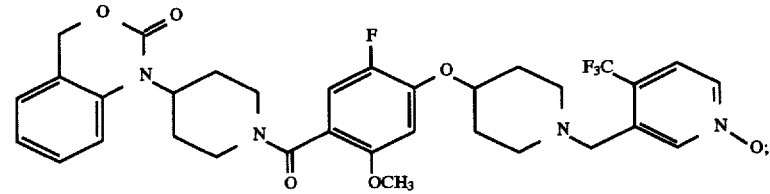

or a pharmaceutically acceptable salt thereof.

5. The compound of claim 1, wherein W is

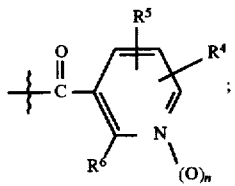

$R^3$ is selected from hydrogen of $C_{1-4}$ alkoxy;

$R^4$, $R^5$ and $R^6$ are each independently selected from hydrogen, straight chain $C_{1-4}$ alkyl or trifluoromethyl;

or a pharmaceutically acceptable salt thereof.

6. The compound of claim 5, wherein $R^1$ and $R^2$ are each independently selected from hydrogen of fluorine;

$R^3$ is $C_{1-4}$ alkoxy; and $R^4$, $R^5$ and $R^6$ are each independently selected from hydrogen, straight chain $C_{1-4}$ alkyl or trifluoromethyl;

or a pharmaceutically acceptable salt thereof.

7. The compound of claim 1, wherein W is

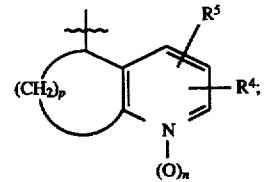

$R^3$ is selected from hydrogen or $C_{1-4}$ alkoxy;

$R^4$ and $R^5$ are each independently selected from hydrogen, straight chain $C_{1-4}$ alkyl or trifluoromethyl;

or a pharmaceutically acceptable salt thereof.

8. The compound of claim 7, wherein $R^1$ and $R^2$ are each independently selected from hydrogen of fluorine;

$R^3$ is $C_{1-4}$ alkoxy; and $R^4$ and $R^5$ and each independently selected from hydrogen, straight chain $C_{1-4}$ alkyl or trifluoromethyl;

or a pharmaceutically acceptable salt thereof.

9. The compound of claim 8, wherein W is elected from

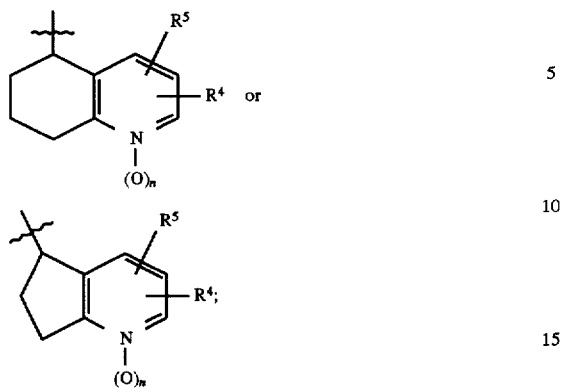

pharmaceutically acceptable salt thereof.

10. The compound of the formula

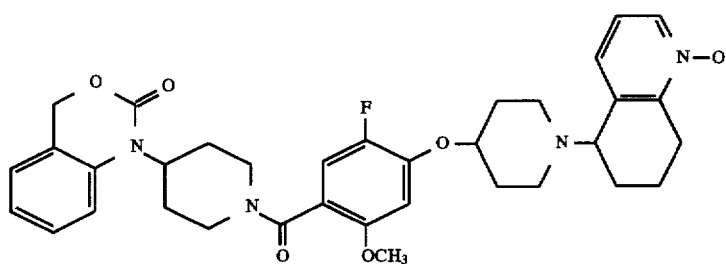

or a pharmaceutically acceptable salts thereof.

11. A pharmaceutical composition comprising a pharmaceutically acceptable carrier and a therapeutically effective amount of the compound of claim 1.

12. A pharmaceutical composition comprising a pharmaceutically acceptable carrier and a therapeutically effective amount of the compound of claim 7.

* * * * *